United States Patent [19]

Van Sickle

[11] Patent Number: 4,713,472

[45] Date of Patent: Dec. 15, 1987

[54] PREPARATION OF DIMETHYL 4,4′-STILBENEDICARBOXYLATE AND INTERMEDIATES THEREFOR

[75] Inventor: Dale E. Van Sickle, Kingsport, Tenn.

[73] Assignee: Eastman Kodak Company, Rochester, N.Y.

[21] Appl. No.: 863,274

[22] Filed: May 15, 1986

[51] Int. Cl.⁴ .................... C07C 69/76; C07C 67/313; C07C 67/32
[52] U.S. Cl. ....................... 560/53; 528/308; 560/64; 560/66; 560/76; 560/96
[58] Field of Search ............. 560/53, 64, 66, 96, 560/76; 528/308

[56] References Cited

U.S. PATENT DOCUMENTS 4,276,430  6/1981  Reller et al. ................. 560/66
4,399,298  8/1983  Sugimori et al. ............. 560/66
4,546,197  10/1985  Bateman et al. ............. 560/66

*Primary Examiner*—Werren B. Lone
*Assistant Examiner*—Vera C. Clarke
*Attorney, Agent, or Firm*—Thomas R. Savitsky; William P. Heath, Jr.; J. Frederick Thomsen

[57] ABSTRACT

The preparation of 4,4′-dimethylstilbenedicarboxylate by acetylating 4,4′-bis(methoxycarbonyl)benzoin to give 4,4′-bis(methoxycarbonyl)benzoin acetate, selectively reducing 4,4′-bis(methoxycarbonyl)benzoin acetate with hydrogen to give 1,2-bis(4-methoxycarbonylphenyl)ethanol, and subjecting the 1,2-bis(4-methoxycarbonylphenyl)ethanol to either (1) dehydration or (2) acetylation to 1,2-bis(4-carbomethoxyphenyl)-1-acetoxy ethane followed by pyrolysis thereof to give the 4,4′-dimethylstilbenedicarboxylate. In this process, the new compounds 4,4′-bis(methoxycarbonyl)benzoin acetate, 1,2-bis(4-methoxycarbonylphenyl)ethanol, and 1,2-bis(4-carbomethoxyphenyl)-1-acetoxy ethane are produced and the novel preparations thereof are performed.

10 Claims, No Drawings

PREPARATION OF DIMETHYL 4,4'-STILBENEDICARBOXYLATE AND INTERMEDIATES THEREFOR

DESCRIPTION

This invention concerns the preparation of the dimethyl ester of 4,4'-stilbenedicarboxylic acid, hereinafter referred to as (DMSC), and novel intermediates thereof, which (DMSC) is a desirable monomer for certain polyester compositions which have special utility in performance engineering plastic applications, such as the polymers described in U.S. Pat. Nos. 4,414,382; 4,420,602; 4,468,510; 4,526,822 and 4,459,402. The best known preparation of this ester material involves the dehydrodimerization of toluic acid with sulfur and subsequent esterification of the acid; however, alternative approaches are desirable to avoid the extensive sulfur contamination and unacceptably low yields associated with this synthesis.

The present process involves the preparation of (DMSC) by selective reduction of the novel intermediate 4,4'-bis(methoxycarbonyl) benzoin acetate, hereinafter (BEA), to the novel intermediate 1,2-bis(4-methoxycarbonylphenyl)ethanol, hereinafter (BME), and subsequent dehyration of this intermediate to the present (DMSC) product. In a variation of this process, the hydroxyl of (BME) is esterified and the novel tri-ester (TRE) then pyrolyzed to give the (DMSC).

A practical overall reaction scheme for preparing the aforesaid intermediates and the (DMSC) product, a portion of which scheme embodies the present invention, using typical agents and reactants, is as follows wherein Reaction 1 is the known preparation of the benzoin diester (BDE) from methylformylbenzoate (MFB):

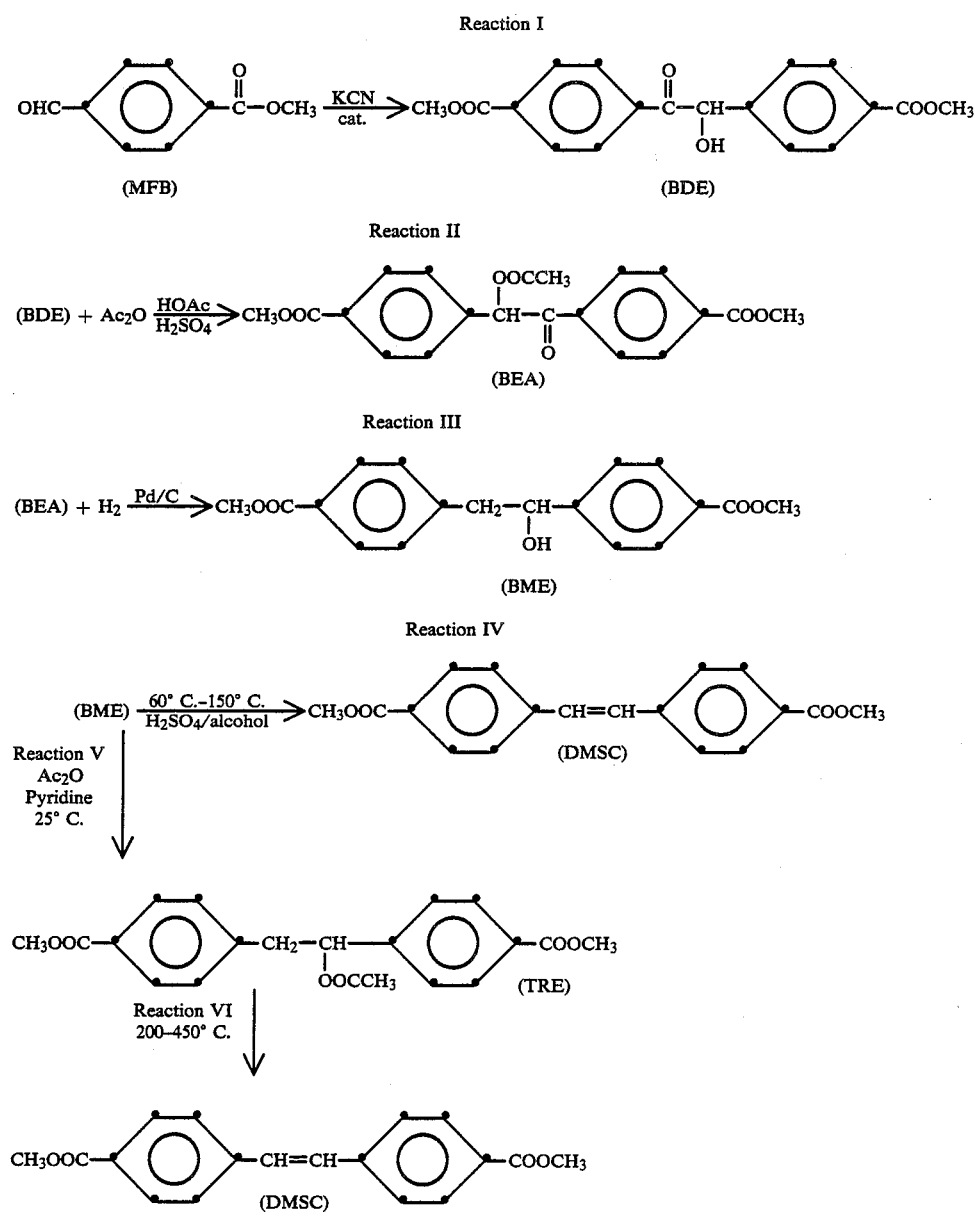

In this scheme, reactions V and VI represent an alternative but less preferred route to (DMSC) from (BME).

In reaction I, methyl 4-formylbenzoate (MFB) is self-condensed in typical fashion with potassium cyanide catalyst to produce the corresponding benzoin diester 4,4'-bis(methoxycarbonyl) benzoin (BDE) according to the procedure of the following example:

EXAMPLE 1

A mixture of 368 g of (MFB) of 89% purity, and 900 ml of methanol was warmed gently to dissolve the (MFB), and 10 g of potassium cyanide then added. The resulting dark red mixture was stirred for approximately 10 minutes, and allowed to stand overnight. The mixture was then filtered and the solid (BDE) recrystallized from isopropyl alcohol to give 258 g (79%) of (BDE), mp 143°-145°. The structure was confirmed by infrared analysis and NMR spectroscopy.

In reaction II, conversion of the benzoin diester (BDE) to the benzoin diester acetate (BEA) is according to the procedure of the following example:

EXAMPLE 2

Benzoin diester (BDE) 3280 g, was stirred at about room temperature into a mixture of 4,000 ml acetic acid and 2,144 g acetic anhydride. Two hundred milliliters of concentrated sulfuric acid were added dropwise to the stirring mixture and an exotherm raised the temperature to 41° C. The reaction system was then heated to 80° C. and held at that temperature for 20 minutes. During the hold period, the color changed to reddish orange. The mixture was cooled to 25° C. and poured slowly into a vigorously stirred slurry of 32 pounds of ice in four gallons of water. The reactor was rinsed with 200 ml acetic acid into the slurry. The solids were collected on a vacuum filter and then reslurried and refiltered three times, each time with five gallons of water. The crude product (vacuum dried) weighed 3,610 g (yield: 97.5%) and had a melting point of 112°-115° C. The (BEA) structure was confirmed by NMR analysis. This (BEA) product (1,800 g) was stirred into 12,000 ml of ethanol, the resultant slurry then heated to reflux to complete dissolution, then cooled to 10° C. and then stirred for one hour while the slurry temperature fell to 6° C. The solids were collected on a vacuum filter and washed twice, each time with 500 ml of ethanol chilled to about 5° C. After vacuum drying, the (BEA) product, melted at 117–122° C. and weighed 1,676 g (93% recovery). The (BEA) structure was confirmed by NMR analysis.

In reaction III, the benzoin ester acetate (BEA) is carefully and selectively hydrogenated at pressures, for example, of up to about 100 psig, to the (BME) rather than to the compound

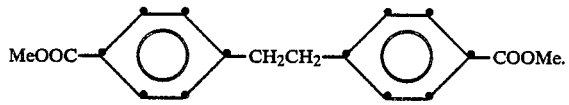

Useful catalysts are described in *Catalytic Hydrogenation, Techniques and Applications in Organic Synthesis*, Robert L. Augustine, 1965, Marcel Dekker, Inc., New York, p. 44, and *Catalytic Hydrogenation Over Platinum Metals*, P. N. Rylander, Acedemic Press, New York, 1967, pp. 274–287 and 449–454. In order to insure proper hydrogenation of the (BEA) to (BME) structure rather than to the (CH$_2$CH$_2$)moiety it is preferred (1) to use a palladium catalyst wherein the ratio of Pd metal to (BEA) is from about 0.0001 to about 0.025, preferably from about 0.0003 to about 0.007, (2) the Pd is on a suitable support such as carbon, alumina or the like, (3) the temperature is from about 50° C. to about 70° C., (4) the H$_2$ pressure is from about 1 to 5 atmospheres, most preferably 1 to 3 atmospheres, and (5) the system is maintained in a substantially nonacidic condition, and most preferably in a basic condition. Lower or high H$_2$ pressures may be used but to no practical advantage.

In reaction IV, the (BME) is dehydrated to give the (DMSC) by any of the conventional techniques such as described in Chapter 5 of *Advanced Organic Chemistry*, Fieser & Fieser, Reinhold, 1961, and on pages 888 and 889 of *Comprehensive Organic Chemistry*, Barton and Ollis, Vol. 6, Pergamon Press, Oxford, England.

In reaction V of the alternate route, the (BME) is acetylated by any suitable means such as with Ac$_2$O in the presence of pyridine to the triester (TRE) according to the following example:

EXAMPLE 3

A mixture of 2.0 g of (BME), 1.0 g of acetic anhydride, and 10 ml of pyridine was allowed to stand at room temperature overnight. The mixture was poured into 100 ml of water wherein the crude (TRE) gum precipitated and crystallized. The collected (TRE) crude product when washed further with water and dried, weighed 2.2 g. Recrystallization of the crude product from 20 ml of ethanol yielded 1.68 g of white crystals, melting approximately 95°-98° C. and assaying better than 95% pure (TRE) by NMR analysis.

In reaction VI, the (TRE) is pyrolyzed to (DMSC) at temperatures of from about 200° to about 450° C. in accordance with techniques such as described in "*Pyrolytic Methods in Organic Chemistry*," Roger F.C. Brown, Academic Press, 1980, New York, pp. 85–89, 112.

The overall process of the present invention is defined as the the process for preparing 4,4'-dimethylstilbenedicarboxylate (DMSC) comprising acetylating 4,4'-bis(methoxycarbonyl)benzoin (BDE) to 4,4'-bis(methoxycarbonyl)benzoin acetate (BEA), hydrogenating the 4,4'-bis(methoxycarbonyl)benzoin acetate to 1,2-bis(4-methoxycarbonylphenyl)ethanol (BME), subjecting the 1,2-bis(4-methoxycarbonylphenyl)ethanol to either (1) dehydration at from about 20° C. to about 250° C. to produce the 4,4'-dimethylstilbenedicarboxylate, or (2) acetylation to produce 1,2-bis(4-carbomethoxyphenyl)-1-acetoxy ethane (TRE) which is then pyrolyzed at from about 200° C. to about 450° C. to produce the 4,4'-dimethylstilbenedicarboxylate.

In this process, the new compounds (BEA), (BME), and TRE are produced and the novel preparations thereof are performed as described in detail herein.

In the acetylation of BDE to (BEA), the dehydration of (BME) to (DMSC), the acetylation of (BME) to TRE and the pyrolysis (acetic acid elimination) of TRE to (DMSC) can all be carried out under conditions well known to those skilled in the art for similar reactions and the examples of these reactions given herein employ typical conditions. It is noted, however, that the H$_2$SO$_4$/alcohol mixture for the dehydration of (BME) to (DMSC) in molar ratios of from about 1 to about 0.05 give the best results in regard to product color and purity. In the dehydration, temperatures of from about 20° C. to about 250° C. can be used, but preferably are from about 60° C. to about 150° C. for the H$_2$SO$_4$/methanol system. It is also preferred that the pyrolysis of (TRE) be carried out at between about 250° C. and 350° C.

The following example further describes the practice of the present invention.

EXAMPLE 4

HYDROGENATION OF (BEA) to (BME)

The (BEA) (18.5 g., 0.05 mole) was mixed with 100 ml of ethanol, 7.6 g. of triethylamine (acid acceptor, not critical but preferred) and 1.0 g. of 5% palladium-on-charcoal catalyst and stirred under 45 psig of hydrogen at 60° C. until no more hydrogen was absorbed by the mixture. The hydrogen uptake was quite close to the required 0.10 mole. The product solution was brought to a boil, some additional ethanol added (50 ml) and the hot mixture filtered to remove the hydrogenation catalyst. Upon cooling to room temperature white crystalline product precipitated which, upon collection and drying, weighed 11.86 g. This product analyzed 90-95% (BME) by NMR spectroscopy. An additional 1.78 g. of product analyzing 85-90% purity is obtained by evaporation of the filtrate, water extraction of the solid product and collection of the insoluble residue.

EXAMPLE 5

DEHYDRATION OF (BME) TO (DMSC)

A 1.0 g. sample of the 90-95% pure (BME) is held at 225° C. for 6 hours in the presence of 10 mg. of p-toluenesulfonic acid. At the end of this period the solid cake product is dissolved in 15 ml of boiling methyl benzoate; the solution is filtered hot to remove a small amount (0.06 g.) of insoluble material. Upon cooling the desired product precipitates which, after collection, washing with ethanol and drying weighs 0.65 g. This final product (DMSC) is identical with material prepared as described in the literature (Beilstein, 9, E III, 4595) and has an uncorrected melting point of 235° C. to 237° C.

A preferred dehydration is as follows: A mixture of 10 ml of sulfuric acid and 50 ml of alcohol, e.g. methanol or isopropanol or mixtures thereof (strong exotherm), is prepared and 1.00 g of (BME) is dissolved in this mixture by boiling and swirling. The solution is set on the steam bath and the methanol allowed to slowly boil away, during which time, white crystals of product precipitates from the solution. The heating is maintained for about six hours before the product is collected by filtration on a fritted glass funnel and washed repeatedly with methanol. The weight of the dried product was 0.92 g (97.6%) and the product melts at 240°-241° C. (uncorrected) and assays 98.5% pure by gc area percent. The NMR spectrum is consistent with the proposed (DMSC) structure and 95+% purity. In some larger-scale dehydrations where product purities are lower, recrystallization of the crude material from methyl benzoate achieves adequate purification.

The invention has been described in detail with particular reference to preferred embodiments thereof, but it will be understood that variations and modifications can be effected within the spirit and scope of the invention.

I claim:

1. The process for preparing 4,4'-dimethylstilbenedicarboxylate comprising acetylating 4,4'-bis(methoxycarbonyl)benzoin to 4,4'-bis(methoxycarbonyl)benzoin acetate, hydrogenating 4,4'-bis(methoxycarbonyl)benzoin acetate to 1,2-bis(4-methoxycarbonylphenyl)ethanol, subjecting the 1,2-bis(4-methoxycarbonylphenyl)ethanol to either (1) dehydration at from about 20° C. to about 250° C. to produce the 4,4'-dimethylstilbenedicarboxylate, or (2) acetylation to produce 1,2-bis(4-carbomethoxyphenyl)-1-acetoxy ethane, which is then pyrolyzed at from about 200° C. to about 450° C. to produce the 4,4'-dimethylstilbenedicarboxylate.

2. The process of claim 1 wherein the hydrogenation is carried out between about 50° C. and about 70° C. in a solvent, in the presence of a palladium catalyst wherein the Pd/4,4'-bis(methoxycarbonyl)benzoin acetate weight ratio is from about 0.0001 to about 0.025, and at a hydrogen pressure of from about 1 to about 5 atmospheres, wherein the reaction system is maintained in substantially a non-acidic condition.

3. The process of claim 2 wherein the hydrogenation solvent is selected from ethanol, methanol and n-propanol or mixtures thereof.

4. The process of claim 2 wherein the dehydration is done in a H2SO4/alcohol mixture at a molar ratio of from about 1 to about 0.05 at a temperature of from about 60° C. to about 150° C.

5. The process of claim 2 wherein the hydrogenation catalyst metal is Pd in a weight ratio with respect to 4,4'-bis(methoxycarbonyl)benzoin acetate of from about 0.0003 to about 0.007, and the Pd is supported on charcoal or alumina.

6. The process of claim 2 wherein the H2 pressure is maintained at from about 1.0 to about 3.0 atmospheres.

7. The compound of the formula

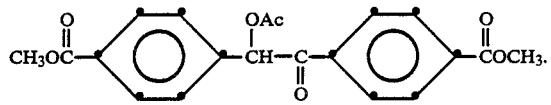

8. The compound of the formula

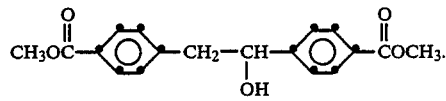

9. The compound of the formula

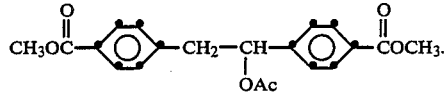

10. The process comprising pyrolyzing the compound of claim 9 at a temperature of from about 200° C. to about 450° C. to produce the compound

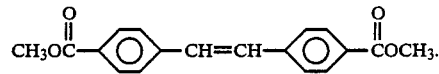

* * * * *